United States Patent [19]

Isaacs et al.

[11] 4,181,882

[45] Jan. 1, 1980

[54] CORROSION MONITORING APPARATUS

[75] Inventors: Hugh S. Isaacs, Shoreham; John R. Weeks, Stony Brook, both of N.Y.

[73] Assignee: The United States of America as represented by the United States Department of Energy, Washington, D.C.

[21] Appl. No.: 916,624

[22] Filed: Jun. 19, 1978

[51] Int. Cl.² ............................................. G01N 27/00
[52] U.S. Cl. ............................. 324/71 R; 324/65 CR
[58] Field of Search ................. 324/29, 30 R, 65 CR, 324/71; 204/195 R, 1 T, 195 C

[56] References Cited

U.S. PATENT DOCUMENTS

| | | | |
|---|---|---|---|
| 2,714,190 | 7/1955 | Pflasterer | 324/65 CR |
| 3,633,099 | 11/1972 | Richman | 324/71 R |
| 4,065,373 | 12/1977 | Martin | 204/195 C |
| 4,087,742 | 5/1978 | Khoo | 324/65 CR |
| 4,098,112 | 7/1978 | Kramer | 324/65 CR |

*Primary Examiner*—M. Tokar
*Attorney, Agent, or Firm*—R. V. Lupo; Leonard Belkin

[57] ABSTRACT

A corrosion monitoring device in an aqueous system which includes a formed crevice and monitoring the corrosion of the surfaces forming the crevice by the use of an a-c electrical signal.

23 Claims, 6 Drawing Figures

CORROSION MONITORING APPARATUS

BACKGROUND OF THE INVENTION

This invention was made under, or during, the course of a contract with the United States Department of Energy.

The present invention relates to apparatus for monitoring and detecting the onset of rapid corrosion in aqueous systems.

In what might be called normal corrosion, metal surfaces within a corrosive operating system environment are relatively uniformly attacked. This is the least serious and most easily tolerated form of corrosion and the operating system may be specifically designed to account for its effects. Moreover, a variety of techniques and apparatus have been developed for monitoring corrosion and measuring its rate in low temperature non-boiling systems.

More rapid corrosion may occur non-uniformly in a system and can cause failure of the corrodible structure in a very short time with little warning. Extremely high rates associated with specific types of non-uniform corrosion or pitting, such as that taking place in crevices and cracks, make it impractical to design to take the same into account. Corrosion test probes and measurement techniques developed for conditions of uniform surface corrosion have been found to be unsatisfactory when applied to the detection of crevice corrosion at high temperatures or during boiling at the surfaces.

Corrosion in both nuclear and fossil fueled steam generators is generally a consequence of the presence of aggressive impurities introduced into the coolant system through condenser leakage. Crevice corrosion develops as the particulate impurities concentrate in regions of the steam generator protected from coolant flow, as for example in crevices or under deposited corrosion products, and adjacent to heat transfer surfaces. The combination of each of these factors—the concentration of aggressive impurities, the configuration of the restricted or crevice area, and the presence of heat transfer surfaces—appears to be responsible for precipitating the onset of particularly rapid crevice corrosion.

Inasmuch as the development of rapid corrosion is not predictable and consequently the operating system cannot be designed to tolerate such conditions, the same must be suppressed before significant or appreciable structural damage occurs. An indication that the conditions within the steam generator or other operating system are such as to be particularly conducive to the onset of rapid corrosion prior to its development or significant progression therein would give the operator time to take corrective action to thereby prevent or minimize its effects. Such corrective action could, for example, take the form of reducing the critical concentrations of impurities in the coolant or aqueous solution.

The apparatus suggested by the prior art for monitoring corrosion is generally unsatisfactory for the purpose of detecting the development of rapid corrosion in a steam generator system application. As typified by U.S. Pat. No. 3,331,021 to Marsh et al No. 3,406,101 to Kilpatrick and No. 3,788,962 to Frenck, the prior art teaches the use of three probes—consisting of power, specimen and reference electrodes—inserted into a corrosive electrolytic solution. The relative corrosive conditions of the probes are externally monitored by way of direct electrical connections to the electrodes.

In a nuclear or fossil fueled steam generator, however the use of separate specimen electrodes inserted into the same may be unreliable or otherwise impractical. In addition, the lack of an available reference electrode which is highly stable for sufficient lengths of time between planned outages of the system renders these prior art teachings unsuitable for application to steam generator systems.

Prior art apparatus directed particularly toward the detection of crevice corrosion merely disclose test probe structures which include an electrode provided with a crevice or otherwise restricted area. Such art is typified by U.S. Pat. No. 3,042,863 to Marsh et al, No. 3,633,099 to Richman, and No. 3,599,090 to Fitzpatrick et al, wherein it is taught to measure the relative change in resistance between "normal" and crevice-containing electrodes inserted into an electrolyte as indicative of the onset of crevice corrosion. These probes have been found to be unsatisfactory for use with a steam generator system where factors such as the presence of heat exchange surfaces in the generator may cause rapid corrosion to develop thereon well before corrosion of the crevice-containing electrode causes measurable changes in probe resistance.

It is, therefore, the desideratum of the present invention to provide for the early detector of conditions for the initiation of rapid corrosion in a closed aqueous system prior to the development or significant progression of corrosion therein so as to enable immediate corrective action to be taken to prevent or minimize the effects of such corrosion. Specifically, it is an object to provide a device for insertion into a closed aqueous system, the device being so configured as to be more conducive to the onset of rapid corrosion than the internal structural members of the closed system, and a method of monitoring the insertion device for indications of the development of rapid corrosion thereon without direct connection of an electrical signal lead to its corrodible structure.

It is a further object of the present invention to provide means whereby both the response due to the solution resistance of the coolant, indicative of the presence of aggressive impurities, and the response due to the corroding surface may be monitored.

It is a still further object of the invention to provide a device for insertion into a closed aqueous system, the device being so configured as to be more conducive to the onset of rapid corrosion and said device comprising a part of the structure of said system.

Further objects, features and advantages of the present invention will be more fully appreciated by reference to the following detailed description of a presently preferred, but nonetheless illustrative, embodiment in accordance with the present invention when taken in conjunction with the accompanying drawings, wherein:

FIG. 1—is an elevation, partly broken away and partly in section, of a corrosion monitoring apparatus constructed in accordance with the teaching of the present invention;

FIG. 2—is a side view of corrosion monitoring apparatus similar to that shown in FIG. 1 wherein an alternate manner of supportably positioning the sensor probes is provided;

FIG. 3a—is an electronic analog of the corroding system in which a corrosion monitoring apparatus according to the present invention is operationally positioned;

FIG. 3b—are the component wave forms developed at the corroding surface and in the coolant respectively;

FIG. 3c—is a composite detected by a corrosion monitoring apparatus according to the present invention; and, FIG. 4—is a semischematic representation of electronics which may be utilized in conjunction with a corrosion monitoring apparatus according to the present invention.

DETAILED DESCRIPTION OF THE PREFERRED EMBODIMENT

High corrosion rates develop in pressurized water reactor steam generators due to the build up of aggressive impurities in restricted areas. Three major factors—the concentration of impurities in the system liquid coolant, the configuration of crevice or similarly restricted or occluded areas about which the coolant is circulated, and the presence of heat transfer surfaces—share the major responsibility for instituting the rapid development of so-called crevice corrosion. Thus, a sudden undetected increase in the concentration of coolant impurities, which may for example be introduced into the system through condenser leakage, can bring about the onset of crevice corrosion with extreme speed and resultant major system structural damage before detection. It is, therefore, essential for the system operator to anticipate internal crevice corrosion before the same develops or significantly proceeds.

Corrosion testing carried out in the operating equipment under actual service conditions provides the most acceptable and reliable method for detection. Prior art devices, however, require that electrical connections be made directly to corrodible sample electrodes under test, and such devices may not be practical or reliable under conditions commonly associated with steam generators and other types of closed aqueous systems.

Underlying the present invention is the recognition that the condition of the surfaces when rapid corrosion develops must be markedly different from those during normal operation and that these changes should be observable using electrochemical techniques. It is further recognized that the onset of these changes may be detected without direct electrical connection to the corrodible surface by passing an electrical signal through the coolant onto the surface and measuring the response of the corroding surface, again through the coolant. A preferred apparatus for accomplishing this procedure will now be fully described.

Figure 1:
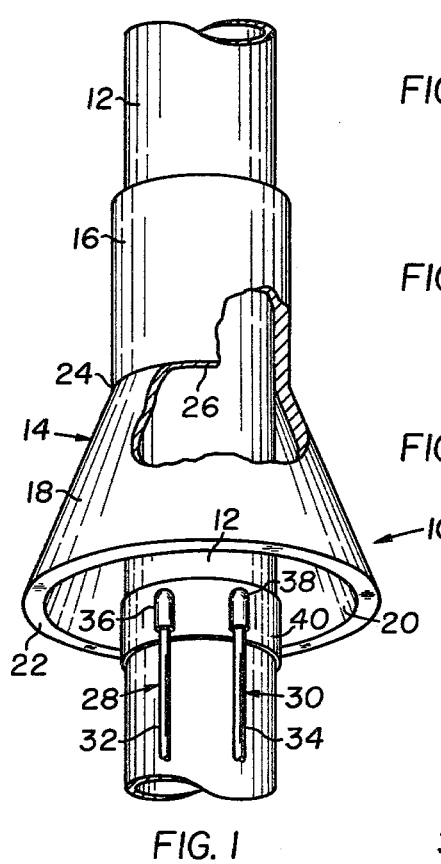

In FIG. 1 is seen an embodiment constructed according to the teachings of the present invention of a crevice corrosion monitoring apparatus, designated by the general reference numeral 10, for placement within a pressurized steam generator or other closed aqueous system. The typical steam generator with which it is intended that the present invention may be utilized includes a pressurized chamber or vessel containing a plurality of heated fixed rods or tubes. A liquid coolant, commonly water, is circulated throughout the chamber to controllably maintain the operating temperature of the system within predetermined limits, the liquid frequently boils locally on contact with the heated tube surfaces. Crevice areas are formed where the tubes pass through the chamber walls and surface and as a result of reduced access of the continuous flow of coolant into such restricted areas, aggressive impurities present in the liquid tend to collect therein. Crevice corrosion often rapidly develops on the tubing surface in these crevice areas as the impurities become concentrated thereon.

Thus, the corrosion monitoring device of the present invention, as embodied in the apparatus 10 shown in the drawings, is so configured as to provide crevice conditions of the same type and general nature as those normally found in a pressurized steam generator but of a more extreme character. That is, the present invention provides what might be called a "worst case" test crevice area configured to concentrate impurities more quickly than crevices normally present in the operating system.

The apparatus 10 is placed into the steam generator pressurized chamber within which the liquid coolant circulates. The apparatus 10 provides structure upon which it is anticipated that rapid crevice-type corrosion will develop prior to or substantially concurrent with the development of such corrosion in the actual system structural components. Inasmuch as the apparatus 10 further provides means for detecting the onset of crevice corrosion thereon, significant corrosive damage to the generator system may be substantially prevented by recognizing that particularly serious corrosion-promoting conditions are present—serious enough to cause rapid corrosion in the apparatus 10. Consequently, the onset of rapid system corrosion can often be anticipated prior to its onset or development, enabling corrective action to be taken to cure the internal corrosion-promoting conditions present before serious damage necessitating a generator shutdown for repairs occurs.

Turning now to FIG. 1, the corrosion monitoring apparatus 10 includes a heated surface which my be in the form of an elongated tubular member 12 of substantially circular cross-sectional configuration. The tube 12 may conveniently be internally heated and in the disclosed steam generator application is preferably formed of "Alloy 600" tubing which is highly resistant to corrosion within the operating system. The selection of a tubular configuration and of "Alloy 600" as the material of construction of the member 12 has been made to conform to the form and substance of the heated tubular internal structural components commonly present in a steam generator system as previously discussed. It should, however, be clear that the configuration of the heated surface and its material of construction is for the most part a matter of design choice at least partially influenced by the structure present in the particular operating system within which the apparatus 10 is to be utilized. Similarly, although it is clear that the presence of a heated surface substantially accelerates the onset of corrosion, the provision of a heated member in the apparatus 10 is not essential to the concept of the present invention; where it is desired to simulate a crevice condition in an operating system not containing members at an elevated temperature, the tube 12 or its equivalent need not be heated.

A steel cap generally designated 14 is fitted encirclingly or otherwise about at least a portion of the tube 12 and is seen to include a sleeve or neck portion 16 and a frustoconical or infundibuliform cup 18 formed integral with or otherwise connected to the sleeve 16. The sleeve 16 may be clamped, welded or adhesively secured in position on the tube 12 or its interior bore selectively sized for a snug, non-slip frictional fit about the member 12. It should be noted that where an adhesive or cement is utilized to positionally fix the sleeve 16 on the tube 12, such adhesive need not be electrically conductive since, unlike the teachings of the prior art, no direct electrical connection is made to the crevice area and thus electrical conductivity between the cap 14 and the tubular member 12 is not required in practicing the present invention. This will become clear as this description proceeds further. As before, the specification of steel as the material of construction of the cap 14 is based upon the common use of steel to fabricate the walls and surfaces of the pressurized chamber in a steam generator and consequently to form a portion of the crevices defined therein. Other metallic materials could be readily substituted for the specified steel and their use would be within the contemplation of the present invention.

It should, therefore, be clear that the cap 14, in combination with the tubular member 12 about which it is encirclingly fixed, forms or constitutes a crevice forming means which includes a crevice or restricted area 20 defined between and bounded by the interior of the tapered cup or collar 18 and the tubular member 12. The crevice 20 is provided with an opening for the entry of circulating liquid at the widened proximal end 22 of the cup 18 and the cross-sectional area of the crevice 20 progressively dimishes therefrom to the cojoinder of the cup distal end 24 with the tubular member 12 at the acutely angular junction 26. As the liquid coolant flows into the crevice area 20, its movement therein is restricted or impeded by the decreasing area of the crevice and it deposits in the crevice any particulate impurities suspended in the liquid. The impurities tend to build up first in the angular junction 26 and thence in the remainder of the crevice area 20 on the surface of the tubular member 12 as more impurities are deposited therein. Corrosion eventually develops on the heated tubular member 12 under the deposited aggressive impurities, initially as "pitting" of the surface.

The tapered configuration of the cup or collar 18 which bounds the outward defines of the crevice area 20 is preferred in that such shape has been found to concentrate impurities in the crevice region significantly more readily than at least the great majority of naturally-occurring crevice areas within typical steam generators. However, those skilled in the art will readily recognize that particular applications may require or indicate advantages to modifying or otherwise changing the structural configuration of the cup 18. Such modifications and substitutions are deemed to be within the scope of the teachings of the invention disclosed herein.

Still referring to FIG. 1, a pair of probes or sensors generally designated 28, 30 is insulatively supported on the tubular member 12. The probes 28, 30 comprise wires 32, 34 which may advantageously be fabricated of zirconium or an alloy thereof and are provided with platinum tips 36, 38 respectively. The zirconium wires 32, 34 act as conductors electrically insulated from the water—and from the supporting tubular member 12—by highly stable and protective oxides, as zirconia, which may be formed on their surfaces for such purposes. In order to prevent their relative shifting or movement, particularly in view of locally significant turbulence that may develop as the liquid coolant boils along the heated tube surface, the wires 32, 34 may be clamped to tube 12 or adhesively or otherwise secured thereto and, if desired, an electrically insulative member (not shown) may be interposed between the wires 32, 34 and the tube 12 to further insure against any possibility of direct electrical connection therebetween.

The positioning of the probe tips 36, 38 is such that the same lie proximate the widened end 22 of the cup 18 and outwardly of the defines of the crevice area 20. The tips 36, 38 are electrically conductive and must be immersed within and electrically communicate with the liquid coolant but must in addition be insulated from direct electrical connection with the tubular member 12. Accordingly, an insulative member 40 can conveniently be adhesively or otherwise interposed between the probe tips 36, 38 and the tube 12. Alternatively, the member 40 could by way of example, be provided as a clamp (not shown) formed of a dielectric material for supporting and retaining the tips 36, 38 insulatively on the tubular member 12. The tips 36, 38 need not be positioned adjacent one another although they are so shown for convenience of illustration.

It should be understood that in the operation of a steam generator or the like, steam or hydrogen bubbles within the system can form or become caught in crevices or in similarly restricted areas therein. Thus, were the tips 36, 38 positioned within the defines of the crevice 20 when such a bubble formed therein, there would be a break in the electrical connection of the monitoring system as the bubble effectively insulated the conductive tips 36, 38 from the circulating liquid coolant. As will be better understood as this description proceeds, such a situation would render the apparatus 10 at least temporarily unable to monitor the corrosive condition of the crevice area 20.

Thus, in addition to the requirement of maintaining the probes 28, 30 insulated from direct electrical connection with the tubular member 12 and the supported cap 14, the probe tips 36, 38 should preferably be positioned outside the defines of the crevice area to prevent steam bubbles from interfering with the operation of the corrosion monitoring apparatus 10. Other criteria related to placement of the probes 28, 30 relative to the tube 12 or cup 18 are not critical and may be modified from that shown in FIG. 1 as desired or dictated by the particular intended application or use.

Figure 2:
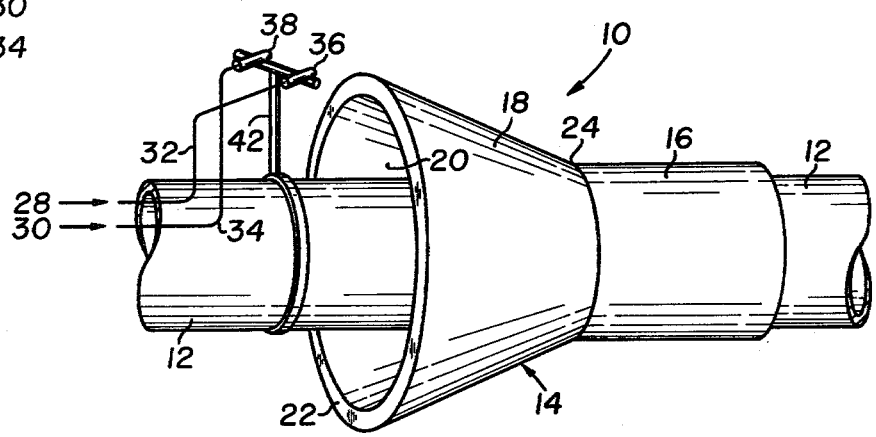

Accordingly, there is shown in FIG. 2 an alternative manner of supportably positioning the probes 28, 30 on the tube 12. In this embodiment of the corrosion monitoring apparatus 10, the conductive tips 36, 38 are positioned spaced from the surface of the tubular member 12 is accomplished in the embodiment of FIG. 2 by supportably mounting the tips 36, 38 on a dielectric T-shaped member 42 which may in turn be clamped about or otherwise secured to the tube 12. All other elements of the FIG. 2 apparatus are identical to those shown in FIG. 1 and described hereinabove and, hence, a description of these elements would be repetitious and redundant and is omitted.

In use, an electrical signal is passed from one probe conductive tip across the surrounding liquid to the metal surface of the tubular member 12 in the crevice area 20. The second probe tipe carries no signal but acts as a sensing electrode by which the electrical response of the corroding surface is measured, again through the liquid. Corrosion on the tubular member 12 forms an interface region between the underlying metal and the liquid, and an analysis of the response of the corroding interface to the impressed electrical excitation enables the onset of rapid corrosion to be electrochemically detected.

Preferably, the electrical excitation is provided by an applied AC square current wave. The use of an alternating current wave obviates the need for a reference electrode stable over long periods of time, enables particular ease of measurement over very short time frames and provides for electrical monitoring without influencing or interfering with the corrosive processes taking place. As will be discussed, the AC technique further allows local solution conductivity to be measured concurrent with monitoring of interface condition.

Use of a square wave also provides advantages in its incorporation of a wide range of frequencies or time dependencies of processes at the surface. A current wave, an opposed to an applied potential wave, simplifies the analysis of the results which can be performed, inter alia, by studying the response curve and comparing and balancing the same with an analog of a capacitor and resistor in parallel circuit connection.

Figure 3A:
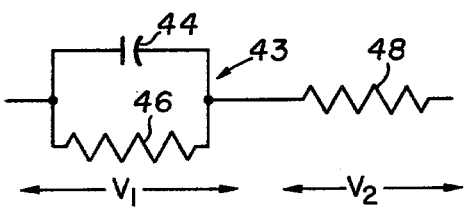

Thus, an AC square current wave is impressed on one of the probes and the potential response of the corroding interface is measured from the other. Generally, the potential response of the test surface to an applied current wave allows an impedance across the test surface to be determined. This impedance may be expressed in terms of an analog parallel resistance-capacitance network 43 in series with the liquid or solution resistance, as shown in FIG. 3a.

Since the interface in reflecting a potential or voltage response to the applied current wave exhibits a time dependence, the electrical representation of the interface must incorporate a capacitance in the analog. Capacitor 44 in FIG. 3a represents this capacitance of the electrochemical double layer. A resistor 46 connected across the capacitor 44 may be related to, for example, the corrosion rate. This single resistance-capacitance network 43 constitutes a substantial simplification and other capacitance or pseudo-capacitance may be required to more accurately represent the interface, depending upon the nature of the information sought and the precision of measurement necessary or desired.

The solution resistance exhibits no time dependencies and responds immediately to current changes in the AC wave as would a series resistor; a resistor 48 is thus provided in series with the network 43 to represent the liquid or solution resistance. Hence, the two parts of the interface—the network 43 and the resistor 48—give clearly separable potential responses to the applied AC current wave as shown respectively by $V_1$, designated by the numeral 50, and $V_2$, designated 52, in FIG. 3b. The sum of the separate potential wave-forms $V_1$ and $V_2$ yields the observed response, designated 54 in FIG. 3c.

Figure 3B:
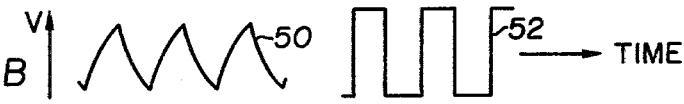
Figure 3C:
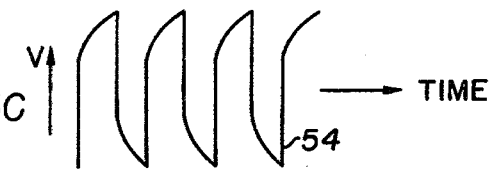

Inasmuch as the use of an applied square wave provides a square wave response from the solution resistance 48, this response can be subtracted from the observed wave-form 54 to obtain the separate responses shown in FIG. 3b. The magnitude of the response $V_2$ is directly proportional to the solution resistance and may, therefore, be utilized to measure the conductivity of the liquid between the probes and the crevice. The conductivity decreases as impurities build up on the crevice area and, thus, such measurement offers an early indication of impurity concentration changes which might lead to the development of rapid corrosion.

The impedance characteristics of the interface, as represented by the parallel network 43, depend upon the reactions there taking place and other properties of the metal surface. At low frequencies the analysis is simplified as the resistance component 46 of the interface is the same as the slope of a linear polarization measurement—$dV/dI$, the differential resistance, where $dV$ is the changes in potential and $dI$ is the change in current. When the anodic and cathodic currents are low, the corrosion and kinetic processes at the surface are slow giving a high resistance. When the corrosion rates are high, there is in effect a large leakage current across the interface and the resistances are low. Hence, any major reduction in the resistance 46 would indicate the onset of corrosion.

Figure 4:
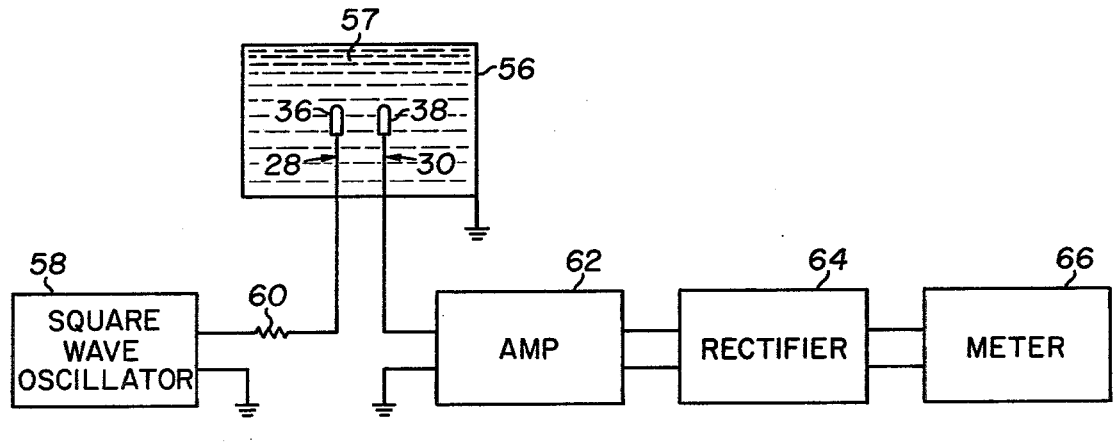

Exemplary electronics for utilizing the corrosion monitorint apparatus 10 to detect the onset of corrosion is shown in the semischematic representation of FIG. 4, in which the reference numeral 56 is used to designate the pressurized generator system closed chamber or vessel substantially filled with a liquid 57. The probe tips 36, 38 are shown free from and without the remaining physical structure of the apparatus 10 for ease of illustration and to facilitate understanding of the electrical circuit alone.

A signal generator or square wave oscillator 58 of well-known construction connected in series with ahigh resistance 60 may be employed to produce the preferred square current wave. The resistor 60 is connected to the first probe 28 so as to impress the AC current waveform on its conductive tip 36 from which, as previously discussed, the wave is passed through the surrounding liquid 57 to the corrodible metal surface. The second probe tip 38 which senses the potential response of the surface is connected to a differential amplifier 62 in which compensation for the series solution resistance may be provided to remove the non-time-dependent component of the observed response. The chamber 56 and the signal generator 58 and amplifier 62 are connected to a common ground. The output of the differential amplifier is then connected to a rectifier 64 and thence to a meter 66. The onset of corrosion is indicated when the meter reading drops below a predetermined value. Calibration of the present invention is not crucial since the change in output is expected to be very large (i.e., greater than 50%) with the onset of rapid corrosion.

The applied AC square current wave may range in frequency from one hertz to as high as one megahertz, although to simplify the analysis and obviate the consideration of other relaxation phenomenon at high frequencies a frequency of approximately 200 hertz is preferred. The magnitude of the current wave utilized may be anywhere from a single microamp to approximately 100 milliamps RMS, depending upon the resistance offered by the interface and the distance of the probes 28, 30 from the crevice area, since increasing the probe-crevice distance will increase the resistance caused by the liquid. This distance, and any necessary increase in current to compensate therefor, is not however critical in that the major changes that take place when corrosion begins are still easily detected in the manner taught. However, the conductive probe tips 36, 38 should be kept relatively small and be positioned sufficiently closely to the crevice area 20 so that a substantial portion of the applied current wave flows to the apparatus 10 within the crevice area 20, so that the sensed response is substantially influenced by the initiation of corrosion within crevice 20.

It will be readily understood by those skilled in the art that the manner of use of the corrosion monitoring apparatus 10 shown in FIG. 4 represents but a single exemplary implementation and is not meant to constitute a limitation on the detection circuits with which the apparatus 10 may be utilized. The selection and design of auxiliary electronics therefor is, of course, somewhat dependent upon the particular application considered.

Although the corrosion monitoring apparatus 10 has been particularly described in terms of its use in a pressurized water reactor steam generator, it should be clear that it is equally applicable to the detection of rapidly developing corrosion in a substantially endless variety of aqueous systems. Such systems may utilize water or any other electrically conductive liquid or electrolytic or operating solution. It is within the contemplation of the invention to configure selectively the various elements of the apparatus 10 so as to simulate "worst case" crevice conditions in any operating system within which it is desired to anticipate the development of rapid corrosion.

Likewise, the concept of the present invention is broad enough to encompass the creation of a crevice area directly on a structural member of the operating system rather than placing within the system intentionally simulative test structure. Thus, in the particular disclosed use within a steam generator, the tubular member 12 could be one of the plurality of heated tubes already present in the pressurized chamber and the cap 18 would then be fixed on the tube to monitor and detect the rapid development of crevice corrosion thereon before significant damage occurs.

The within teaching of creating a test crevice for the purpose of instigating the onset of rapid corrosion is intended to embrace the creation of any occluded or restricted or roughened area or region where corrosion is likely to develop non-homogenously or non-uniformly. The particularization in the embodiment described of a tapered crevice region including a heated surface is accordingly shown by way of example only and is not deemed to limit the scope or concept of the invention. As such, the teaching herein is notably directed conceptually toward the creation within an operating system of a test crevice region wherein the development of non-uniform corrosion is facilitated and of a manner of monitoring the corrosive condition of the crevice area without direct electrical connection thereto. In the particular disclosed application, the monitoring apparatus 10 provides an early warning of locally active corrosion in high temperature water, even under the highly agitated conditions of local boiling.

A latitude of modification, change and substitution is intended in the foregoing disclosure and in some instances some features of the invention will be employed without a corresponding use of other features. Accordingly, it is appropriate that the appended claims be construed broadly and in a manner consistent with the spirit and scope of the invention herein.

What is claimed is:

1. In a system including surfaces and a liquid coolant containing aggressive impurities in communication with the surfaces, wherein impurities tend to cause corrosion of the surfaces, apparatus for anticipating the onset of corrosion in the system comprising:
   a. crevice forming means for placement within the system in communication with the liquid coolant,
   b. at least a portion of said crevice forming means having a test crevice defined thereon,
   c. first probe means positioned in the liquid coolant proximate said test crevice and spaced therefrom for supplying an AC electric wave and for injection of the electric wave through the liquid coolant substantially to said test crevice,
   d. and second probe means positioned in the liquid coolant proximate said test crevice and spaced therefrom for receiving a responsive electric wave from said crevice forming means through the liquid coolant;
   e. said first and second probe means being insulated from direct electrical connection with said crevice forming means, and said test crevice being so positioned on said crevice forming means as to concentrate impurities more rapidly than crevices on the system surfaces so as to enable the determination of corrosion on said crevice forming means prior to and in anticipation of the development of corrosion in the surfaces of the system by monitoring the resultant electric wave received by said second probe for significant changes in the magnitude of said resultant wave indicating the onset of corrosion to permit corrective action to be taken in advance of significant corrosive damage to the system.

2. The apparatus according to claim 1, the injected electric wave being an AC current wave.

3. The apparatus according to claim 2, the injected AC electric current wave being a square wave.

4. The apparatus according to claim 3, the frequency of the injected AC square wave being in the range of one hertz to one megahertz and preferably being 200 hertz.

5. The apparatus according to claim 1, said crevice forming means comprising a heated tubular member and a collar positioned about at least a portion of said tubular member so as to define said test crevice therebetween.

6. The apparatus according to claim 5, said collar being substantially funnel shaped and having an opening defined at its wider end to concentrate an accumulation of impurities in said test crevice.

7. The apparatus according to claim 6, said first and second probe means being positioned adjacent the collar opening and outside of the defines of said test crevice.

8. The apparatus according to claim 1, each of said first and second probe means comprising a zirconium wire having a platinum tip.

9. The apparatus according to claim 1 said crevice forming means being electrically common to the structure of said system.

10. In a method of monitoring the onset of corrosion in a system including a circulating liquid, the steps of:
   a. forming a crevice on a surface positioned in the system in communication with the circulating liquid;
   b. passing an AC electric wave through the circulating liquid to the crevice by positioning a first electrode proximate the crevice and spaced therefrom for carrying the electric wave and for injecting the same into the circulating liquid, the first electrode being insulated from direct electrical connection with the crevice;
   c. detecting the electrical response of the crevice to the electric wave by positioning a second electrode proximate the crevice and spaced therefrom for receiving the electrical response through the circulating liquid, the second electrode being insulated from direct electrical connection with the crevice and;

d. monitoring the electrical response received by the second electrode for changes in the response indicating the onset of corrosion in the system.

11. In the method according to claim 10, wherein the surface in the system is a tubular member, said step of forming a crevice comprising positioning a collar encirclingly about the tubular member to define therebetween a crevice.

12. In the method according to claim 11, the collar being tapered in configuration.

13. In the method according to claim 12, the first and second probes being positioned external to said tapered collar and spaced therefrom.

14. In the method according to claim 10, the AC electric wave being a square wave.

15. In the method according to claim 14, the AC electric square wave being a current wave.

16. In the method according to claim 15, the electrical response being detected as a voltage potential, such that a drop in the magnitude of the voltage potential below a predetermined value is indicative of the onset of corrosion.

17. In the method according to claim 15, the frequency of the AC electric square wave being in the range of one hertz to one megahertz and preferably being 200 hertz.

18. In the method according to claim 10, the surface on which a crevice is formed being heated.

19. In a method of detecting the presence of conditions capable of initiating the development of corrosion in an operating system which includes therein a liquid, the steps of:
   a. forming a crevice area by positioning a collar in supported relation on and encircling about at least a portion of an elongated tubular member to define a substantially constricted crevice area bounded by surfaces of the collar and tubular member.
   b. exposing the crevice area to corrosive conditions in the operating system by immersing the crevice area in the liquid therein;
   c. positioning first and second electrically conductive probes external to the crevice area and adjacent thereto in communication with the liquid and electrically insulated from direct electrical connection with the collar and tubular member;
   d. impressing a symmetrical wave electrical signal on the first probe to pass the signal through the liquid and onto the surfaces bounding the crevice area;
   e. electrically monitoring the second probe to observe an electrical signal responsive to the impressed signal from the surfaces bounding the crevice area through the liquid, such that substantial variations in the responsive signal over an extended length of time manifests the onset of corrosion on at least a surface bounding the crevice area and thus indicates the presence in the operating system of conditions capable of initiating the onset of corrosion therein.

20. In the method according to claim 19, the elongated tubular member being heated.

21. In the method according to claim 20, the collar being frustoconically configured so as to define the crevice area with an enlarged open end tapering to a connection of the collar with the tubular member at the reduced diameter end of the collar.

22. In the method according to claim 21, the step of positioning the first and second probes including fixing the probes in supported relation on the elongated tubular member adjacent the enlarged open end of the tapered collar.

23. In the method according to claim 19, the impressed symmetrical wave being an AC square wave.

* * * * *